(12) United States Patent
Kopreski

(10) Patent No.: US 7,588,548 B2
(45) Date of Patent: Sep. 15, 2009

(54) ENDOTHERMIC BANDAGE WITH DISPENSER FOR THE TREATMENT OF BURNS AND OTHER INJURIES

(76) Inventor: Michael C. Kopreski, 23 Wellington Dr., Long Valley, NJ (US) 07853

(*) Notice: Subject to any disclaimer, the term of this patent is extended or adjusted under 35 U.S.C. 154(b) by 375 days.

(21) Appl. No.: 11/403,338

(22) Filed: Apr. 13, 2006

(65) Prior Publication Data
US 2007/0027415 A1 Feb. 1, 2007

Related U.S. Application Data

(60) Provisional application No. 60/674,085, filed on Apr. 22, 2005.

(51) Int. Cl.
*A61F 13/00* (2006.01)
(52) U.S. Cl. .............. 602/2; 206/441; 607/96; 607/112
(58) Field of Classification Search .......... 607/96, 607/108–112; 602/2, 48, 41–43, 54
See application file for complete search history.

(56) References Cited

U.S. PATENT DOCUMENTS

| | | | |
|---|---|---|---|
| 2,017,570 A * | 10/1935 | Pollak | 225/52 |
| 3,977,202 A | 8/1976 | Forusz et al. | |
| 4,011,945 A * | 3/1977 | Bourne et al. | 206/223 |
| 5,190,033 A | 3/1993 | Johnson | |
| 5,310,402 A * | 5/1994 | Rollband | 602/42 |
| 5,431,622 A * | 7/1995 | Pyrozyk et al. | 602/2 |
| 5,697,961 A | 12/1997 | Kiamil | |
| 5,887,437 A | 3/1999 | Maxim | |
| 5,984,951 A | 11/1999 | Weiss et al. | |
| 6,755,852 B2 | 6/2004 | Lachenbruch et al. | |
| 2005/0080368 A1* | 4/2005 | Hurwitz | 602/2 |

OTHER PUBLICATIONS

Burns, 2002, 28:173-176, (To Follow).
Mil. Med. 2002, 167:939-943, (To Follow).
Nguyen, Nhu Lam, Richard T. Gun, Anthony L. Sparnon & Philip Ryan, "The Importance of Immediate Cooling—a Case Series of Childhood Burns in Vietnam", *Elsevier Science Ltd*, 2002, pp. 173-176. (To Follow).
Sawyer, Thomas W., PhD, "Therapeutic Effects of Cooling Swine Skin Exposed to Sulfur Mustard", *Military Medicine*, vol. 167, Nov. 2002, pp. 939-943. (To Follow).

* cited by examiner

*Primary Examiner*—Kim M Lewis
(74) *Attorney, Agent, or Firm*—Davis & Bujold, P.L.L.C.

(57) ABSTRACT

This invention provides methods of treating thermal burns, chemical burns, and other injuries by a bandage within which is activated an endothermic chemical reaction upon withdrawal of the bandage from a dispenser. The endothermic bandage thereby provides a cooling treatment effect for a burn or injury. The easily portable dispenser contains an endothermic bandage that can be cut or separated in varying size, dependent upon the size and extent of the burn or injury.

20 Claims, 2 Drawing Sheets

ENDOTHERMIC BANDAGE WITH DISPENSER FOR THE TREATMENT OF BURNS AND OTHER INJURIES

This application is a continuation-in-part of U.S. Provisional Application Ser. No. 60/674,085 filed Apr. 22, 2005, the entire disclosure of which is hereby incorporated by reference herein.

BACKGROUND OF THE INVENTION

This invention relates to a bandage that when used provides a self-contained endothermic chemical reaction that produces a cooling treatment effect beneficial for burn injuries and for other injuries such as injuries of the muscles and joints. The invention further encompasses a bandage dispenser that enables storage of the bandage and promotes activation of the endothermic reaction within the bandage when the bandage is withdrawn from the dispenser. The invention thereby provides a portable bandage applicable to wounds of varying size, whose endothermic cooling effect is particularly beneficial for the treatment of skin burns, and further beneficial for treatment of other injuries such as but not limited to chemical injuries to the skin, muscular injuries, joint injuries such as sprains, and contusions.

Burns of the skin are common thermal injuries that range in severity from the first degree burn such as associated with sunburn, to second degree or partial thickness burns characterized by blistering, to full-thickness or third degree burns that can be life threatening and often require skin grafting. Cooling of the affected skin immediately upon burn injury reduces the extent of tissue damage following thermal injury, and thus immediate cooling of the burn is an important component of appropriate first aid for a burn. In a recent study, Nguyen et al. estimated a 32% reduction in the need for skin grafts in burned children when immediate cooling of the injury was applied (*Burns*, 2002, 28:173-176). The rapidity that cooling treatment is instituted is an important determinant of the benefit gained in reducing thermal injury. In the household and emergency room, common cooling first aid treatment includes irrigating or submerging the burn wound in cold water or ice water for a period of time. However, such immediate measures may prove impractical or unavailable for injuries depending upon size and location of the burn, immediate availability to cold water, or during transportation to the hospital. There is thus a need for a method and product that is portable and readily available, enables rapid cooling of the burned skin, and is readily adaptable to the variability of burn injuries in size, extent, and body region affected.

The treatment of injuries such as but not limited to muscular injuries, joint and ligament injuries such as sprains, and other soft tissue injuries such as contusions with the application of cold to reduce swelling and bleeding is well established in medical practice.

In addition, Sawyer et al. recently reported that cooling of skin might also provide beneficial treatment of skin exposed to chemical weapon injuries, such as exposure to vesicant agents (*Mil. Med* 2002, 167: 939-943). Sawyer et al. found post-decontamination cooling of the skin lessened the severity of sulfur mustard induced injury.

Several patents in the prior art have addressed cooling bandages or packs for injury, for example, U.S. Pat. Nos. 5,984,951; 6,755,852; 5,697,961 and 5,190,033; including those based upon endothermic chemical reactions, for example U.S. Pat. Nos. 5,887,437; and 3,977,202; the above art incorporated herein in their entirety. However, cooling bandages and packs described in the prior art often have significant limitations such as requirements that they be maintained in cold storage prior to use, thereby limiting their use in the field, or limitations in their adaptability to varying injury due to their fixed size and bulkiness. The prior art does not provide a convenient endothermic bandage within a portable dispenser suitable for burns and other injuries of varying size and body location through the use of a variable size bandage, as is provided by the invention herein.

SUMMARY OF THE INVENTION

The present invention provides methods for an endothermic cooling bandage that is contained within a dispenser, whereupon an endothermic chemical reaction is activated upon withdrawal of the bandage from the dispenser, said endothermic bandage thereby enabling a cooling treatment to be applied to burn injuries of the skin, chemical injuries to the skin, muscular and joint injuries, contusions, and other soft tissue injuries. In a particularly preferred embodiment, the invention provides a cooling treatment to thermal burns of the skin, including first, second, and third degree burns. In another preferred embodiment, the invention provides a cooling treatment to muscular and joint injuries, and to contusions. In another preferred embodiment, the invention provides a cooling treatment to chemical injuries to the skin, including but not limited to chemical weapons injuries and chemical vesicant injuries to the skin.

The invention provides a method wherein an endothermic chemical reaction is activated within a bandage upon withdrawal of the bandage from a dispenser, thereby producing a bandage that enables application of a cooling treatment; the steps of the method comprising the combining of two or more chemical agents upon withdrawal of the bandage from a dispenser; the combination of two or more chemical agents thereby activating an endothermic chemical reaction within the interior of the bandage that results in cooling the bandage; the bandage thereby enabling application of a cooling treatment.

In one preferred embodiment of the inventive steps, the chemical agents necessary for production of the endothermic reaction exist upon the surface of two separate layers located within the dispenser which are thereby combined within the dispenser upon withdrawal of the bandage to both form the endothermic bandage and activate an endothermic chemical reaction, wherein each of the two chemical-treated surfaces are thereby situated within the interior of the endothermic bandage product, thereby providing for an endothermic chemical reaction within the interior of the bandage.

In one aspect of the embodiment, the separate layers are further adjoined using an adhesive, whereby the edges of the layers comprising the bandage are thereby sealed together.

In another aspect of the embodiment, the layers having separate chemical surfaces are maintained within the dispenser within separated rolls until combined to form the endothermic bandage product.

In another aspect of the embodiment, the chemicals on the surface of the separate layers are further separated from each other by protective coverings upon their surface, and/or by a partition within the dispenser.

In another preferred embodiment of the inventive steps, two or more chemical agents are located within the interior of a preformed bandage, wherein one or more of the chemical agents are separated from the other(s) within a capsule or compartment, said capsule or compartment being ruptured when the bandage is withdrawn from the dispenser, thereby activating an endothermic chemical reaction within the interior of the endothermic bandage that results in cooling the bandage; the bandage thereby enabling application of a cooling treatment.

In one aspect of the embodiment, the capsule or compartment separating one or more chemical agents is mechanically ruptured during withdrawal of the bandage from the dispenser. In one aspect, mechanical rupture is accomplished by passing the bandage through rollers.

In one aspect of the embodiment, capsules separate one or more chemical agents, wherein the capsules release the chemical agents in a time-dependent fashion upon exposure to the solvent, thereby permitted a prolonged period of cooling to occur.

The methods of the inventive steps provide for the endothermic bandage product to be applicable to burns, wounds, and injuries of varying size and extent, whereby the bandaged is dispensed in varying length and size, the method comprising the steps of dispensing the bandage from the dispenser, and cutting the dispensed bandage to a length and size that varies with the size and extent of the burn, wound, or injury.

In one embodiment, the dispenser comprises in part a blade or cutting edge suitable for cutting the bandage.

In one embodiment, the endothermic bandage is segmented to comprise sections to facilitate the cutting or division of the bandage.

In one aspect of the embodiment, the segmentation of the bandage to facilitate the cutting or division of the bandage thereby creates separate repetitive sections of the bandage wherein the endothermic chemical reaction occurs, wherein the cutting or separating of the bandage between two repetitive segments thereby determines the length and size of the bandage upon use.

In a preferred embodiment, the endothermic bandage product is self-adherent to facilitate attachment to the body.

In a preferred embodiment, the endothermic bandage product includes an antiseptic surface or otherwise medicated surface.

In a preferred embodiment, the endothermic bandage is packaged within the dispenser under sterile or antiseptic conditions.

In a preferred embodiment, a bandage for the treatment of a chemical agent injury to the skin is provided, wherein the bandage provides a cooling treatment effect through an endothermic chemical reaction. In one aspect of the embodiment, the endothermic chemical reaction is activated upon withdrawal of the bandage from a dispenser.

DETAILED DESCRIPTION OF THE INVENTION

The invention provides methods for an endothermic cooling bandage that is contained within a dispenser until use. Upon withdrawal of the bandage from the dispenser, an endothermic chemical reaction is activated resulting in cooling of the bandage, thereby enabling a cooling treatment to be provided by the bandage. The endothermic cooling bandage is thereby particularly applicable for the treatment of burns of the skin, muscular injuries, joint injuries, and contusions. The bandage has particular utility in the first aid treatment of thermal burns of the skin including first, second, and third degree burns, and is particularly advantageous in minimizing the extent of tissue damage from severe burn injuries, such as from second and third degree burns. The endothermic bandage is further particularly applicable for the treatment of chemical injuries to the skin, including in particular but not limited to chemical weapons injuries such as vesicant agent injuries of the skin. One such vesicant injury for which the endothermic bandage is advantageous is following exposure of the skin to sulfur mustard. The invention is further advantageous as a first aid treatment that is beneficial in reducing swelling and bleeding associated with muscular injuries, joint injuries, and contusions.

The invention provides for an endothermic cooling bandage that is within a portable dispenser, and is thus advantageous for use in circumstances where cold clean water or refrigeration methods or other methods of cooling may not be available or feasible. The endothermic bandage with dispenser is thus particularly advantageous for use in the field or in the ambulance, but remains further advantageous for use in the home, in the emergency care facility, and in the hospital and physician's office.

In the practice of the methods of the invention, the endothermic bandage or its components are stored within a dispenser, most preferably wherein the bandage or its components are maintained in a sterile or antiseptic condition until use. It is to be recognized that both the endothermic bandage product and the dispenser comprise aspects of the present invention. Upon withdrawal of the endothermic bandage from the dispenser, an endothermic chemical reaction is initiated by the combining of two or more chemical agents within the bandage, resulting in cooling of the bandage. The endothermic bandage thereby cools to a temperature preferably between 33 degrees Fahrenheit and 57 degrees Fahrenheit, and most preferably between 40 degrees Fahrenheit and 45 degrees Fahrenheit, whereby a cooling treatment may be provided to burns, wounds, and injuries.

Figure 1:
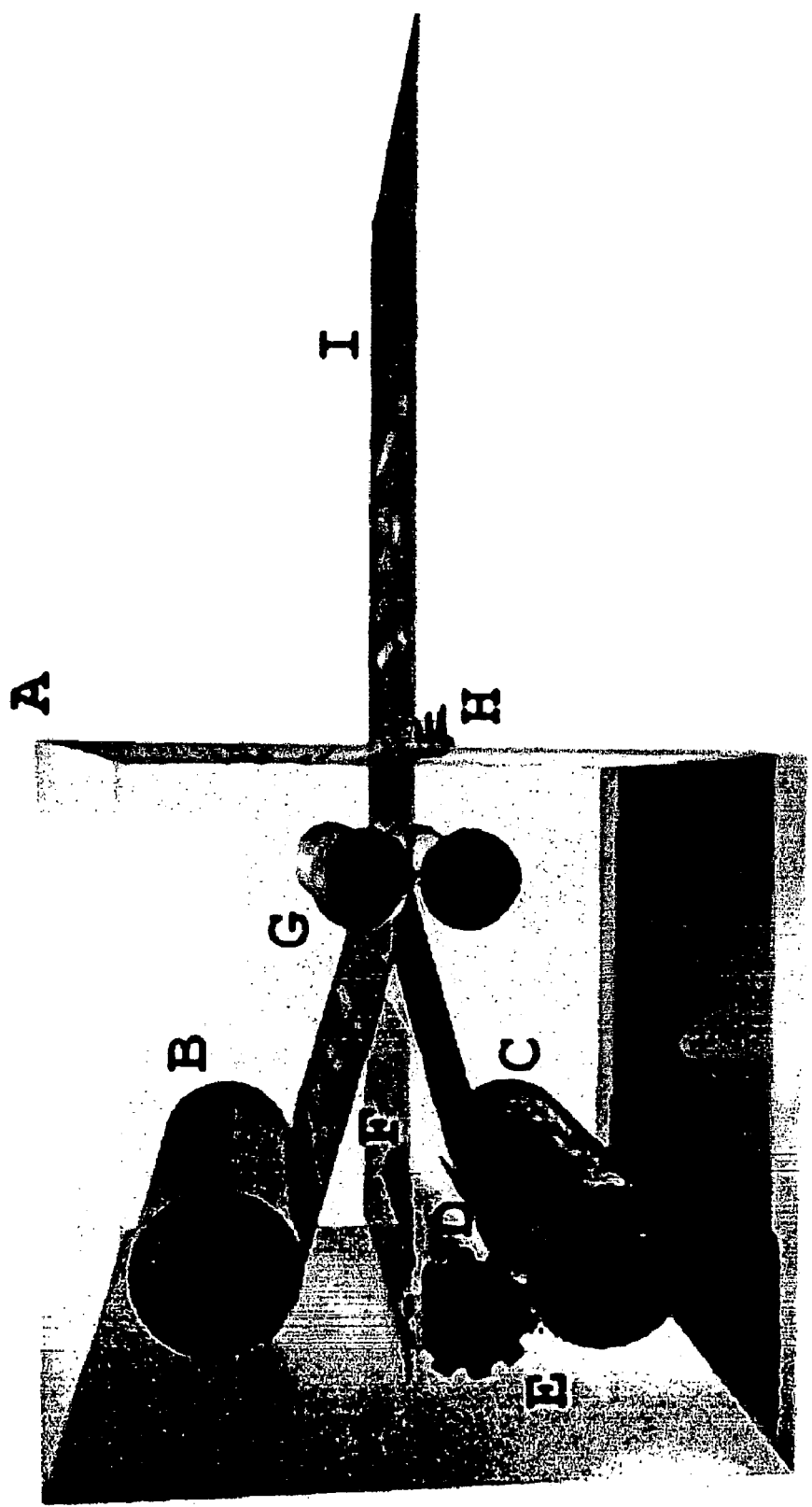
FIG. 1 is a schematic diagram of the endothermic bandage dispenser interior in a preferred embodiment of the inventive methods. The components of the dispenser are identified as follows: letter A identifies the dispenser casing or container; B identifies one layer of the bandage, upon the surface of which are one or more chemical agents needed for the endothermic chemical reaction to occur, hereinafter referred to as the Y-chemical layer, further shown both rolled and as the unrolled layer; C identifies one layer of the bandage, upon the surface of which are one or more chemical agents needed for the endothermic chemical reaction to occur, hereinafter referred to as the X-chemical layer, further shown both rolled and as the unrolled layer; D identifies a protective layer collection spool which aids in removing and collecting any surface protective covering placed upon a chemical layer prior to combining of the Y-chemical layer with the X-chemical layer; E identifies a gear whereupon by turning a chemical roll upon withdrawal of the bandage, herein shown as the X-chemical layer roll, the protective layer collection spool (D) is thereby turned; F identifies a partition that prevents accidental exposure of the Y-chemical layer (B) to the X-chemical layer (C), or chemicals thereof, prior to formation of the bandage and activation of the endothermic chemical reaction; G identifies sealers or rollers that aid in combining the Y-chemical layer (B) and X-chemical layer (C) together to form the endothermic bandage, and further aid in the proper adhesion of the edges of the individual chemical layers with each other to properly seal the edges of the endothermic bandage; H identifies a blade or cutting edge to allow cutting of the bandage from the dispenser; I identifies the endothermic bandage (also referred to herein as the endothermic bandage product) withdrawn from the dispenser.

In a particularly preferred embodiment of the inventive steps, the chemical agents that yield an endothermic chemical reaction when combined are found within a dispenser, as shown in FIG. 1, wherein at least one of said chemicals is located on the surface of a layer that comprises the bandage in part (FIG. 1, Y-chemical layer B), and another of said chemicals is located on the surface of a layer that comprises the bandage in part (FIG. 1, X-chemical layer C). Chemical agents that when combined induce an endothermic chemical reaction are well known within the art, and particularly preferred chemical agents applicable to the inventive steps are ammonium nitrate and sodium acetate trihydrate and ethylene glycol. It is to be understood that other chemical agents known by the art to produce endothermic chemical reactions may alternatively be applied to the inventive steps, including but not limited to other salt compounds and other alkaline aqueous glycol, including those that consist of two to four carbon atoms. In a particularly preferred embodiment, salt compounds such as ammonium nitrate and sodium acetate trihydrate are located on the surface of one layer that comprises the bandage (for example, FIG. 1 and FIG. 2, Y-chemical layer B). In a particularly preferred embodiment, an alkaline aqueous glycol such as ethylene glycol is located on the surface of another layer that comprises the bandage (for example, FIG. 1 and FIG. 2, X-chemical layer C), such as by soaking the glycol in pads or sponges comprising the layer C. Both chemical layers that will comprise the bandage may be stored within the dispenser as rolls until use (FIG. 1, B and C). Upon the combining or joining of the two chemical layers to form the endothermic bandage product, both chemical surfaces would form the interior of the endothermic bandage, where upon an endothermic chemical reaction would take place resulting in the cooling of the bandage.

To prevent premature exposure of the chemicals to each other, the dispenser may optionally include a partition (FIG. 1, F), that separates the two layers comprising the bandage until use. To prevent premature exposure of the chemicals to each other, one or more of the chemical layers may further optionally have a protective covering layer upon the chemical surface, which is automatically removed within the dispenser thereby exposing the chemical layer surface prior to the joining of the two chemical layers. A protective covering layer is particularly advantageous if one chemical is in liquid phase or one layer has pads or sponges soaked in a liquid phase chemical, such as ethylene glycol. As the protective covering layer is removed from the chemical layer, it may be collected upon a protective layer collection spool (FIG. 1, D).

Figure 2:
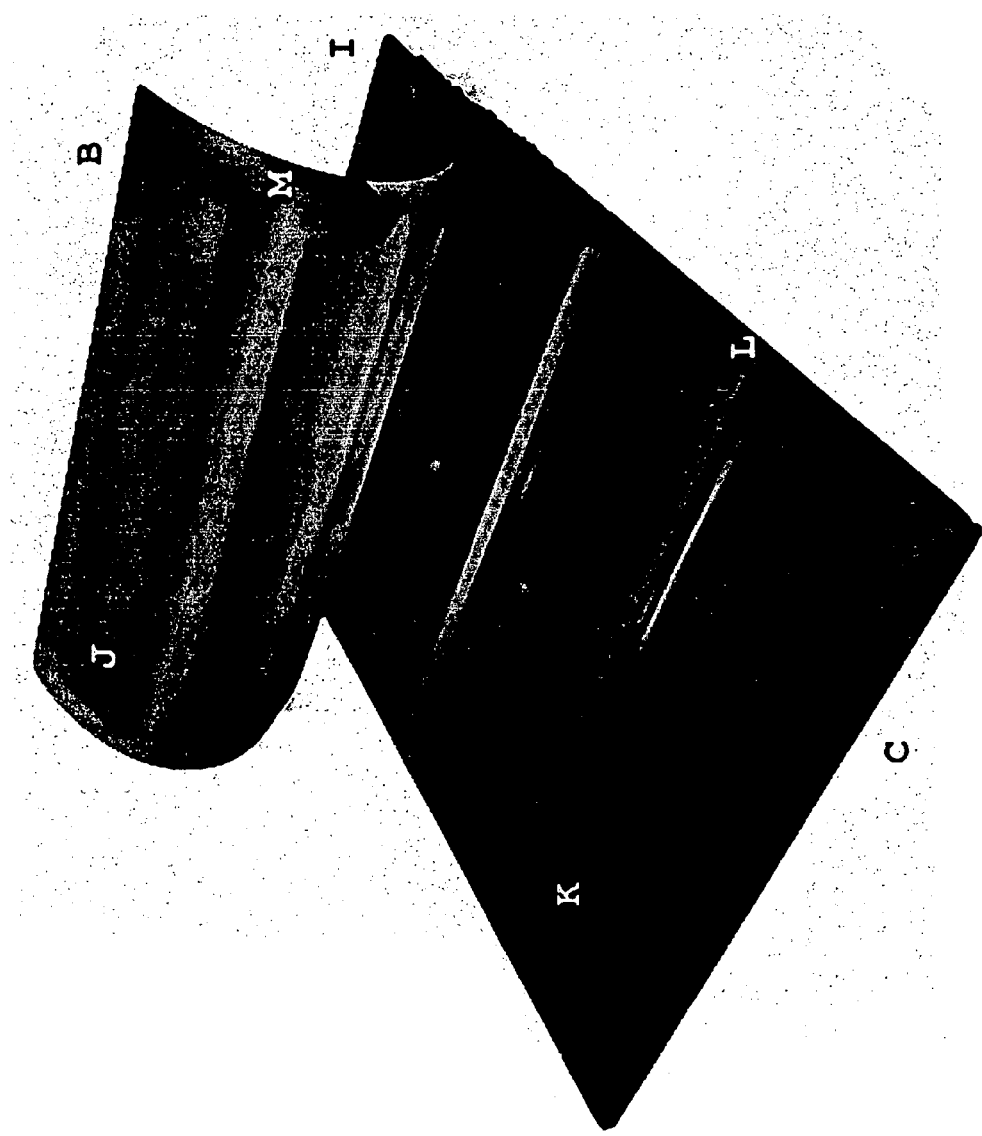
FIG. 2 is a schematic diagram of the endothermic bandage interior in a preferred embodiment of the inventive methods. Letter I identifies the endothermic bandage product; B identifies one layer of the bandage (the Y-chemical layer) upon the surface of which are one or more chemical agents needed for the endothermic chemical reaction to occur; C identifies one layer of the bandage (the X-chemical layer) upon the surface of which are one or more chemical agents needed for the endothermic chemical reaction to occur; J identifies sections on the Y-chemical layer (B) containing one or more chemical agents, wherein sections (J) are further separated by segmented areas of the bandage that allow cutting or division of the bandage; K identifies sections on the X-chemical layer (C) containing one or more chemical agents, wherein sections (K) are further separated by segmented areas of the bandage that allow cutting or division of the bandage; L identifies a sealer adhesive located on the edges and between the K sections of the X-chemical layer (C), said sealer adhesive being one component herein referred to as sealer adhesive 1, of a two component adhesive, wherein said adhesive permits the binding of the edges of layer (C) to layer (B) to form the endothermic bandage (I); M identifies a sealer adhesive located on the edges and between the J sections of the Y-chemical layer (B), said sealer adhesive being a second component herein referred to as sealer adhesive 2, of a two component adhesive, wherein said adhesive permits the binding of the edges of layer (B) to layer (C) to form the endothermic bandage (I).

In the operation of the inventive steps of a preferred embodiment, the endothermic bandage product is withdrawn from the dispenser either manually or mechanically by the user, whereby the separate chemical layers (FIG. 1, B and C) advance through the point of sealers or rollers (FIG. 1, G). As the chemical layers advance within the dispenser, the resulting turn of their rolls (FIG. 1, C) can optionally be utilized to turn the protective layer collection spool (FIG. 1, D) through a gear or gears connecting the chemical layer roll and the protective layer collection spool (FIG. 1, E). Advancement of the chemical layer thereby results in turning of the protective layer collection spool, which thereby facilitates the collection of the protective layer, where upon the protective layer is pulled away from the surface of the chemical layer thereby exposing the chemical layer surface. The two chemical layers (FIG. 1, B and C; FIG. 2, B and C), having exposed chemical surfaces (FIG. 2, J and K), meet at the location of the sealer or roller (FIG. 1, G), where upon the sealer or rollers aid in the combining or joining of the two chemical layers together to form the endothermic bandage product (FIG. 1, I; FIG. 2, I). Upon the meeting of the two chemical surfaces, an endothermic chemical reaction occurs.

In a preferred embodiment, one or both of the separate chemical layers (FIG. 2, B and C) will have an adhesive (FIG. 2., L and M) that aids in the joining of the two separate chemical layers into the final endothermic bandage product. The adhesive thereby insures that the edges of the endothermic bandage are sealed to prevent any leakage or spillage of the chemicals from the bandage interior. In one embodiment, the adhesive is a two compound adhesive, with one compound located on the surface along the side edges and between segmented sections of the X-chemical layer (FIG. 2., sealer adhesive 1; L), and the other compound located on the surface along the side edges and between the segmented sections of the Y-chemical layer (FIG. 2., sealer adhesive 2; M). The two adhesive compounds are compressed together by the sealers or rollers (FIG. 1, G) as the bandage is withdrawn, thus rapidly forming a bond to seal the edge of the bandage. Such adhesive compounds are well known to the art. It is preferred that the layers comprising the bandage be maintained within the dispenser in a sterile or antiseptic manner prior to use.

In another preferred embodiment, a single pre-formed bandage is within the dispenser, wherein two or more chemical agents are located within the interior of the pre-formed or sealed bandage, separated from each other within capsules or compartments of the bandage, wherein the combining of said chemicals result in an endothermic chemical reaction. In the operation of the inventive steps of this embodiment, the bandage is withdrawn from the dispenser either manually or mechanically by the user, whereby the pre-formed bandage advances through rollers within the dispenser that thereby compress the bandage, resulting in rupture of the capsules or compartments containing the chemical agents. The chemical agents thereby mix, whereby an endothermic chemical reaction is initiated within the interior of the bandage resulting in the cooling of the withdrawn endothermic bandage, the bandage thereby enabling application of a cooling treatment. In one aspect of the embodiment, salt compounds are within capsules situated within a liquid-phase chemical reservoir such as but not limited to an ethylene glycol reservoir, wherein the reservoir comprises the interior of the pre-formed endothermic bandage. The salt compounds may be but are not limited to ammonium nitrate and sodium acetate trihydrate. It is to be understood that other chemical agents are known to the art that induce endothermic reactions when mixed, which may be utilized within the pre-formed bandage in this fashion. It is preferred that the pre-formed bandage and/or dispenser be maintained in sterile or antiseptic manner prior to use.

In one aspect of the invention that is applicable to both the single pre-formed bandage embodiments and to those embodiments that comprise the joining of separate chemical layers, the duration of the endothermic reaction may be maintained or prolonged by having one or more chemicals being contained within capsules that degrade or otherwise release their chemical contents in a variable time-release manner upon exposure to solvents or the other constituent chemicals, including those released from other capsules or partitions. For example, the ethylene glycol or other alkaline aqueous glycol could act as a solvent to disrupt the integrity of such capsules in a time-variable manner, resulting for example in variable release of the salt compounds into the ethylene glycol or other solvent.

In a particularly preferred embodiment, the endothermic bandage is segmented into repetitive sections or units in a manner that facilitates the cutting or separating of the bandage from the dispenser at the time of use by enabling the bandage to be cut or separated between two repetitive sections. Each repetitive section or unit includes an interior region where an endothermic chemical reaction can occur. The segmentation allows the bandage to be cut or separated without cutting through sections of the bandage containing chemical agents involved in the endothermic reaction. This design of the bandage thus avoids potential exposure or contamination of the user with the chemical agents found within the interior of the bandage. The position on the bandage of the segment cut or separated thereby determines the length and size of the bandage used following withdrawal from the dispenser. In one embodiment as illustrated in FIG. 2, the segmented design is incorporated into both chemical layers (FIG. 2, B and C), wherein the complimentary regions of each layer meet such that adhesive (FIG. 2, L and M) seal the layers together to create a segmented endothermic bandage product (FIG. 2, I). In other embodiments, segmentation is incorporated into the pre-formed bandage. In preferred embodiments, a blade or cutting edge is in the dispenser (FIG. 1, H) to permit the cutting or detachment of the bandage from the dispenser. It will be recognized that burns and other injuries will be of various sizes, extents, and bodily locations, thereby determining the size requirements of the bandage. It is thus highly desirable that a bandage's length and size can be variable to adapt to the needs of the burn or other injury. The described embodiment is thus highly advantageous in enabling endothermic bandages of varying length and size to be obtained from the dispenser for clinical use.

It is to be recognized that the intended scope of the invention provides for antiseptic creams, gels, lotions, or medicated substances to optionally be applied to the bandage surface such that they may come in contact with the skin upon use. These substances may not only provide therapeutic benefit of their own, but may further promote benefit of the cooling treatment from the bandage to the skin by enhancing conduction.

It is preferred that to achieve maximal clinical benefit, the bandage should cool rapidly to the desired temperature upon withdrawal of the bandage from the dispenser and upon activation of the endothermic chemical reaction. To provide a clinically beneficial treatment cooling effect, the bandage should preferably cool to a temperature between 33 degrees Fahrenheit and 57 degrees Fahrenheit. It is particularly preferred that the bandage cool to a temperature between 40 degrees Fahrenheit and 45 degrees Fahrenheit. It is further preferred that the bandage, once cooled, can maintain its cooling effect for a sufficient period of time to provide adequate treatment benefit. It is thereby preferred that the bandage can provide a cooling effect for a minimum of 30 minutes, and preferably for one hour or more. It is thus most preferred that the bandage incorporate chemical agents that upon endothermic chemical reaction can achieve these conditions of temperature and cooling duration. Chemical agents that can achieve these effects are well known in the art, and include but are not limited to the combination of ethylene glycol, ammonium nitrate, and sodium acetate trihydrate, as described in U.S. Pat. No. 3,977,202, incorporated herein in its entirety.

In a preferred embodiment, the bandage is self-adherent so as to promote maintenance in place of the bandage upon the burn or injury. The bandage may be made self-adherent through the use of exterior coatings of self-adherent material or property, as exemplified by cellophane wraps, or through use of other methods as well known in the art. The bandage may be wrapped around the body region or section affected by the burn or injury, or otherwise cut to size and maintained upon the burn or wound. In one aspect, the bandage may be wrapped in the fashion of an Ace bandage.

It is recognized that the dispenser outer casing may be comprised of various materials, such as but not limited to waxed cardboard, and further packaged in a manner to promote product recognition, instruction on use, and ease of use.

The inventive steps thereby confer particular clinical advantage in the treatment of burns, chemical injuries, muscular injuries, joint injuries, and contusions. The clinical benefit of cooling treatment is well recognized. The inventive steps enable benefit of cooling treatment by enabling immediate first aid care for burns and injuries of varying size and extent.

The methods of the invention and preferred uses for the methods of the invention are more fully illustrated in the following Examples. These Examples illustrate certain aspects of the above-described method and advantageous results. These Examples are shown by way of illustration and not by way of limitation.

EXAMPLE 1

While camping, a 37 year old woman will burn herself by spilling a pot of boiling water onto her leg. She will receive a painful second degree burn of her thigh without treatment. She will immediately seek the endothermic bandage dispenser containing the endothermic bandage, and withdraw from the dispenser the endothermic bandage, obtaining bandage of sufficient length to fully wrap her thigh so that the burned region will be covered. She will take care to cut the bandage from the dispenser, using the dispenser cutting edge, along a clearly marked line corresponding to the bandage segments. Upon withdrawal of the bandage from the dispenser, the woman will notice the bandage is becoming cold due to initiation of an endothermic reaction. She will either apply the bandage to her thigh by herself, or with the assistance of another. The bandage will be self-adherent, and thus easily applied. The bandage will thereby provide cooling treatment and the severity of her burn injury will be minimized. The bandage will provide cooling treatment for at least 30 minutes, during which time the woman will travel to a medical facility to seek further treatment. The physician at the medical facility will find that the bandage is easy to remove and not painful to remove, thereby enabling the easy examination of the burn injury.

EXAMPLE 2

A 22 year old soldier will be exposed to a chemical weapons attack while in the field; thereby he will receive a chemical agent injury from a vesicant agent. The skin on his arms, legs, and trunk will receive injury. He will thereafter receive chemical decontamination. Immediately following decontamination, the endothermic bandage will be withdrawn from the dispenser, thereby activating an endothermic chemical reaction within the bandage. The bandage will thereby provide a cooling treatment effect. Others will wrap the injured body regions of the soldier in the endothermic bandage, and the severity of the chemical injury will thereby be reduced. The bandage will provide a cooling treatment for at least one hour, during which time the soldier will be transported to a medical facility.

EXAMPLE 3

While jogging, a 40 year old man will trip on a street curb and severely sprain his ankle. A neighbor will withdraw the endothermic bandage from its dispenser, whereby an endothermic chemical reaction will be activated resulting in the cooling of the bandage. The man's ankle will be wrapped in the bandage, and the bandage will thereby reduce the amount of swelling and bleeding in the ankle. The man will seek medical attention while the ankle is wrapped in the endothermic bandage.

What is claimed:

1. A method whereby a cooling effect for the treatment of a burn, chemical skin injury, muscular injury, joint injury, or contusion is provided, the method comprising the steps of:
   a) withdrawing a bandage from a dispenser, wherein the bandage is concurrently assembled within the dispenser from separate component parts of the bandage comprising two separate bandage surface layers contained on two separate rolls within the dispenser, wherein one surface layer has at least one chemical on a surface thereof, and wherein the second surface layer includes at least one chemical distinct from the at least one chemical on the first layer, wherein the two surface layers are joined with one another to form a single bandage upon being withdrawn from the dispenser in a manner that results in mixing of the chemicals on both surface layers within an interior of the bandage;
   b) activating thereby an endothermic chemical reaction within the bandage, whereby the bandage is cooled; and
   c) the bandage thereby providing a cooling effect for the treatment of a burn, chemical skin injury, muscular injury, joint injury, or contusion.

2. The method of claim 1, wherein layers that comprise the bandage are joined by an adhesive within the dispenser to produce the bandage.

3. The method of claim 1, whereby the cooling effect is between 33 degrees Fahrenheit and 57 degrees Fahrenheit.

4. The method of claim 1, wherein the bandage withdrawn from the dispenser can vary in length.

5. The method of claim 1, wherein the withdrawn bandage is self-adherent when wrapped around a bodily region.

6. The method of claim 1, wherein the endothermic chemical reaction occurs within segmented sections of the bandage.

7. The method of claim 1, wherein at least one chemical is contained within a capsule or a compartment, where the capsules degrade or otherwise release their chemical contents over time.

8. The method of claim 1, wherein at least one chemical is from the group comprising ammonium nitrate, sodium acetate trihydrate, and ethylene glycol.

9. The method of claim 1, wherein the bandage further provides a gel, lotion, antiseptic cream, or medicated substance to the skin.

10. A method for providing a bandage from a dispenser in which an endothermic chemical reaction can occur, wherein a length or size of the bandage upon use can vary as determined in accordance to clinical need, the method comprising the steps of:
    a) providing a dispenser comprised of two separate rolls of bandage surface layers, wherein each of said layers is segmented into repetitive sections, wherein each of said sections has at least one chemical on or within the surface, wherein distinct chemicals are present on each of the two bandage surface layers; withdrawing the bandage from the dispenser in a manner that the sections of each layer join with one another to form a bandage segmented into repetitive sections; wherein an endothermic chemical reaction occurs within the sections upon the mixing of the chemicals from each surface layer;
    b) thereby enabling that the length or size of the bandage upon use can vary in accordance to the clinical need, wherein the length or size is provided upon the cutting or separating of the bandage between two sections; and
    c) thereby providing a bandage in which an endothermic chemical reaction occurs wherein the length or size of the bandage is determined in accordance to clinical need.

11. The method of claim 10, wherein the clinical need is determined by the extent of a thermal burn.

12. The method of claim 10, wherein the clinical need is determined by a muscular injury, joint injury, or contusion.

13. The method of claim 10, wherein the cutting or separating of the bandage is enabled by a blade or cutting edge within a bandage dispenser.

14. A method for providing a bandage from a dispenser in which an endothermic chemical reaction can occur, wherein a length or a size of the bandage upon use is determined according to the size or extent of a chemical injury to the skin, the method comprising the steps of:
    a) providing a dispenser comprising two separate rolls of bandage layers with each of said bandage layers being segmented into repetitive sections, each of said sections having at least one chemical on or within the section, and distinct chemicals being present on each of the two bandage layers; withdrawing the two bandage layers from the dispenser in a manner that the sections of each of the two bandage layers join with one another to form the bandage by adjoining the two layers together within the dispenser, wherein an endothermic chemical reaction can occur within the sections;
    b) enabling that the length or size of the bandage be determined according to the size or extent of a chemical injury to the skin by cutting or separating of the bandage between repetitive sections; and
    c) thereby the bandage in which the endothermic chemical reaction occurs wherein the length or size of the bandage is determined according to the size or extent of a chemical injury to the skin.

15. The method of claim 14, wherein the cutting or separating of the bandage is enabled by a blade or cutting edge within a bandage dispenser.

16. A method of providing a cooling effect for treating an injury comprising one of a burn, a chemical skin injury, a muscular injury, a joint injury and a contusion, the method comprising the steps of:
- a) providing a first roll which forms a first layer of a bandage within a dispenser, and applying at least one chemical to a first surface of the first layer of the bandage;
- b) providing a second roll within the dispenser, spaced from the first roll, which forms a second layer of the bandage, and applying at least one chemical to a second surface of the second layer of the bandage with the at least one chemical applied to the second surface of the second layer of the bandage being distinct from the at least one chemical applied to the first surface of the first layer of the bandage;
- c) withdrawing a desired length of bandage from the dispenser, when desired, such that the first surface of the first layer mates with the second surface of the second layer and results in formation of a bandage comprising two separate layers and mixing of the at least one chemical of the mating first and second surfaces contained within an interior of the bandage and thereby creating an endothermic chemical reaction within the bandage which cools the bandage; and
- d) applying the bandage to the injury so that the bandage provides a cooling effect for treating the injury.

17. The method according to claim 16, further comprising the step of using an adhesive to join the first and the second layers with one another within the dispenser and form the bandage and the cooling effect of the bandage being between 33 degrees Fahrenheit and 57 degrees Fahrenheit.

18. The method according to claim 16, further comprising the step of cutting the bandage to a desired length, following withdrawal of the desired length of bandage from the dispenser, via a cutting edge carried by the dispenser.

19. The method according to claim 16, further comprising the step of containing the at least one chemical within one of a capsule and a compartment, where upon the rupture of one of the capsule and the compartment promotes activation of the endothermic chemical reaction.

20. The method according to claim 16, further comprising the step of selecting the at least one chemical for the first surface and the second surface from the group comprising ammonium nitrate, sodium acetate trihydrate, and ethylene glycol.

* * * * *